United States Patent [19]

Sawa et al.

[11] Patent Number: 4,469,622

[45] Date of Patent: Sep. 4, 1984

[54] METHOD FOR PREVENTING RUSTING IN SILVER BY USING NOVEL IMIDAZOLE-4(5)-DITHIOCARBOXYLIC ACIDS IN ORGANIC SOLVENT

[75] Inventors: Natsuo Sawa, Tadotsu; Tokuichi Saeki, Onohara, both of Japan

[73] Assignee: Shikoku Chemicals Corporation, Kagawa, Japan

[21] Appl. No.: 460,662

[22] Filed: Jan. 24, 1983

Related U.S. Application Data

[62] Division of Ser. No. 370,354, Apr. 21, 1982, Pat. No. 4,394,511.

[30] Foreign Application Priority Data

Apr. 23, 1981 [JP] Japan .................................. 56-62240

[51] Int. Cl.³ .............................................. C23F 11/16
[52] U.S. Cl. ........................................ 252/391; 422/7
[58] Field of Search ..................... 548/343; 252/391; 106/14.16; 422/7

[56] References Cited

U.S. PATENT DOCUMENTS

| | | | |
|---|---|---|---|
| 2,785,126 | 3/1957 | Scott et al. | 252/391 X |
| 3,772,315 | 11/1973 | Regel et al. | 548/343 |
| 4,357,396 | 11/1982 | Grunewalder et al. | 252/391 X |
| 4,394,511 | 7/1983 | Sawa et al. | 548/343 |

OTHER PUBLICATIONS

Kurata et al., *Chemical Abstracts*, vol. 93, No. 71509d, (1980).

*Primary Examiner*—Benjamin R. Padgett
*Assistant Examiner*—Matthew A. Thexton
*Attorney, Agent, or Firm*—Sherman & Shalloway

[57] ABSTRACT

Disclosed is an imidazole-4(5)-dithiocarboxylic acid compound represented by the following general formula:

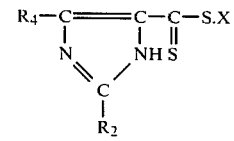

wherein $R_2$ stands for a hydrogen atom or a monovalent hydrocarbon group having up to 20 carbons, $R_4$ stands for a hydrogen atom or an alkyl group having up to 4 carbon atoms, and X stands for a hydrogen atom or an alkali metal atom.

This compound has an excellent rust preventive action to silver. This compound is prepared according to a process which comprises reacting an imidazole compound represented by the following general formula:

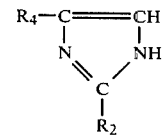

wherein $R_2$ and $R_4$ are as defined above, with carbon disulfides and an alkali metal hydroxide in the presence of a solvent, and if necessary, acidifying the obtained imidazole compound.

1 Claim, No Drawings

METHOD FOR PREVENTING RUSTING IN SILVER BY USING NOVEL IMIDAZOLE-4(5)-DITHIOCARBOXYLIC ACIDS IN ORGANIC SOLVENT

This is a division, of application Ser. No. 370,354, filed Apr. 21, 1982, now U.S. Pat. No. 4,394,511.

BACKGROUND OF THE INVENTION (1) Field of the Invention

The present invention relates to a novel imidazole compound and a process for the synthesis thereof. More particularly, the present invention provides a novel imidazole compound having a rust preventive action to metallic silver.

(2) Description of the Prior Art

It is known that a certain imidazole compound has a rust preventive action to metallic copper (see, for example, Japanese Patent Publications No. 17046/71 and No. 1145/73).

A known imidazole compound such as 2-undecylimidazole or 2-undecyl-4-methylimidazole is effective for preventing rusting in metallic copper, but it does not exhibit any rust preventive action to metallic silver.

SUMMARY OF THE INVENTION

We made researches with a view to finding out an imidazole compound having a rust preventive action to silver, and as the result, we found that an imidazole-4(5)-dithiocarboxylic acid represented by the following general formula:

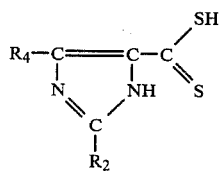

wherein $R_2$ stands for a hydrogen atom or a residue selected from hydrocarbon groups having up to 20 carbon atoms, especially methyl, ethyl, undecyl, heptadecyl and phenyl groups, and $R_4$ stands for a hydrogen atom or an alkyl group having up to 4 carbon atoms, especially a methyl group,
has a rust preventive action to silver.

It must be noted that the above compound has no rust preventive action to metallic copper though it has an excellent rust preventive action to metallic silver. Namely, the above compound has no rust preventive action to copper but discolors copper to a brown color. The reason for this difference between the action to silver and the action to copper has not been elucidated. However, at any rate, it is true that the above compound has a rust preventive action to silver, and this fact is quite interesting.

In accordance with one fundamental aspect of the present invention, there is provided an imidazole-4(5)-dithiocarboxylic acid compound represented by the following general formula:

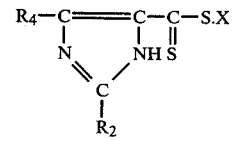

wherein $R_2$ stands for a hydrogen atom or a monovalent hydrocarbon group having up to 20 carbons, $R_4$ stands for a hydrogen atom or an alkyl group having up to 4 carbon atoms, and X stands for a hydrogen atom or an alkali metal atom.

We found that when an alkali metal salt of imidazole is reacted with carbon disulfide in a solvent, a reaction represented by the following formula takes place:

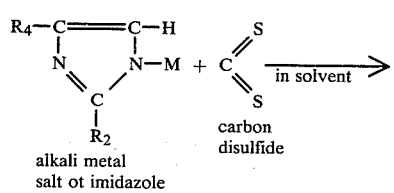

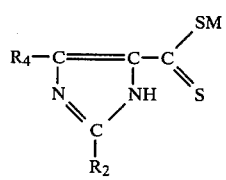

alkali metal salt of imidazole-4(5)-dithiocarboxylic acid

In the above reaction formula, $R_2$ and $R_4$ are as defined above, and M stands for an alkali metal atom.

An alkali metal salt of an imidazole can easily be obtained by heating the imidazole with an equimolar amount of an alkali metal hydroxide while removing water formed by the reaction, and it can also be obtained by heating the imidazole with an equivalent amount of an alkali metal. Since an alkali metal is more expensive than its hydroxide, the latter method is not practically advantageous.

Based on the above finding, we made researches with a view to shortening the process steps and we found that the intended compound can directly be obtained by the one-stage process using an imidazole compound and an alkali metal hydroxide without passing through an alkali metal salt of imidazole according to the following reaction:

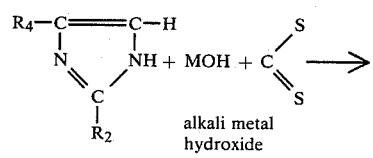

-continued

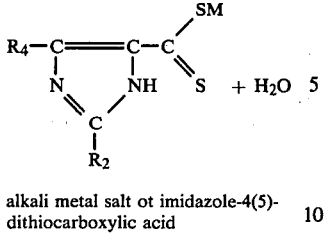

alkali metal salt ot imidazole-4(5)-dithiocarboxylic acid

In the above reaction formula, $R_2$, $R_4$ and X are as defined above.

More specifically, in accordance with another fundamental aspect of the present invention, there is provided a process for the preparation of imidazole compounds represented by the following general formula:

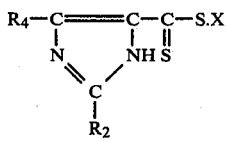

wherein $R_2$ stands for a hydrogen atom or a monovalent hydrocarbon group having up to 20 carbon atoms, $R_4$ stands for a hydrogen atom or an alkyl group having up to 4 carbon atoms, and X stands for a hydrogen atom or an alkali metal atom,
which comprises reacting an imidazole compound represented by the following general formula:

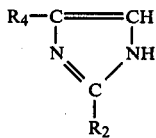

wherein $R_2$ and $R_4$ are as defined above,
with carbon disulfide and an alkali metal hydroxide in the presence of a solvent, and if necessary, acidifying the obtained imidazole compound.

DETAILED DESCRIPTION OF THE PREFERRED EMBODIMENTS

An embodiment of the two-stage process passing through an alkali metal salt will now be described.

In a vessel shielded from carbon dioxide gas in outer air by a soda lime drying tube, 1 mole of an imidazole compound and 1 mole of an alkali metal hydroxide are heated while removing water formed by the reaction from the reaction vessel by distillation. When distillation of water terminates, the reaction product is cooled to obtain 1 mole of the resulting solid alkali metal salt of imidazole. Then, 1 mole of the so-obtained metal salt and at least 1 mole of carbon disulfide are heated and stirred in an appropriate solvent for 3 hours at a temperature higher than room temperature in a reaction vessel equipped with a reflux cooler, a stirrer and a soda lime drying tube, and the reaction mixture is subjected to concentration under reduced pressure to the remove the solvent by distillation, whereby the intended alkali metal salt of the imidazole-dithiocarboxylic acid is obtained in the form of a reddish brown glutinous residue.

In the above reaction, the alkali metal hydroxide may be used in an amount larger than 1 mole. In this case, the reddish brown glutinous residue obtained after removal of the solvent by distillation is a mixture of the alkali metal salt of the imidazole-dithiocarboxylic acid and the alkali metal hydroxide.

An embodiment of the one-stage process using an imidazole, an alkali metal hydroxide and carbon disulfide will now be described. In a reaction vessel equipped with a reflux cooler, a stirrer and a soda lime drying tube, 1 mole of an imidazole, at least 1 mole of an alkali metal hydroxide and at least 1 mole of carbon disulfide are stirred and heated in an appropriate solvent for 3 hours at a temperature higher than room temperature.

Then, the reaction mixture is subjected to distillation under reduced pressure to remove the solvent by distillation, whereby the intended alkali metal salt of the imidazole-dithiocarboxylic acid containing the alkali metal hydroxide is obtained in the form of a reddish brown glutinous residue.

In each of the two-stage process and the one-stage process, dimethylsulfoxide (hereinafter referred to as "DMSO") gives best results as the solvent. Even though other solvents such as water, methanol, ethylene glycol, 1,4-butane diol, t-butanol, pyridine, α-picoline, β-picoline, γ-picoline, aldehydocollidine, triethylamine, acetonitrile, acetone, polyethylene glycol 1500, methylcellosolve, 2-ethyl-4-methylimidazole and DMF are used, better results than those obtained by DMSO cannot be obtained. Among these solvents pyridine, picoline and acetonitrile give yields of about 80%, but these yields are inferior to those attained by DMSO.

When primary alcohols and water are used, formation of an alkali metal salt of xanthic acid preferentially takes place as expected, and advance of the intended reaction is extremely inhibited and the obtained yield is very low.

The solvent is used in an amount of 100 to 600% by weight based on the imidazole.

Ordinarily, 1 to 3 moles of an alkali metal hydroxide and 1 to 2 moles of carbon disulfide are used per mole of the imidazole, but it is preferred that the alkali metal hydroxide and carbon disulfide be used in amounts of 1.5 to 2.0 moles and about 1.2 moles, respectively, per mole of the imidazole.

As the alkali metal hydroxide, there can be used sodium hydroxide and potassium hydroxide, but use of sodium hydroxide is preferred from the economical viewpoint.

The present reaction is an exothermic reaction, and the reaction temperature may optionally be chosen within the range of from room temperature to 150° C. In view of the apparatus problems and the productivity, it is most preferred that the reaction be carried out at 80° to 85° C. In this case, the reaction time is 1.5 to 3 hours.

The present invention may be carried out under pressure. However, since the reaction is sufficiently advanced even under atmospheric pressure, the reaction need not be carried out particularly under pressure.

Then, the obtained alkali metal salt of the imidazoledithiocarboxylic acid is acidified with a mineral acid. This embodiment will now be described.

This alkali metal salt is easily soluble in water, but the dithiocarboxylic acid is hardly soluble in water. By utilizing these solubility characteristics, the latter compound is separated. The alkali metal salt or the alkali metal salt containing the excess of the alkali metal hydroxide is dissolved in water, and active carbon is added to the aqueous solution and filtration is carried out. A mineral acid is added to the filtrate until the filtrate becomes acidic. By this treatment, the alkali metal ion is converted to a mineral acid salt to precipitate the imidazole-dithiocarboxylic acid. The precipitated crystal is recovered by filtration, washed with water and dried to obtain the intended compound. If necessary, the obtained compound may be purified by recrystallization from an organic solvent.

Since the obtained intended compound is easily soluble in aqueous ammonia, if the intended compound is dissolved in aqueous ammonia and the resulting solution is subjected to concentration under reduced pressure to evaporate ammonia, the intended compound is precipitated again in the form of a crystal from the aqueous solution. If this crystal is recovered by filtration, the intended compound can be obtained in the purified form.

The above reaction can be expressed by the following reaction formula:

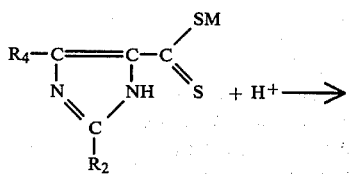

alkali metal salt of
imidazole-dithiocarboxylic
acid

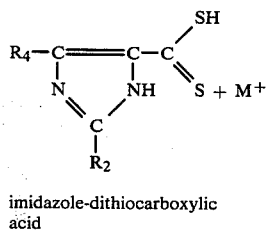

imidazole-dithiocarboxylic
acid

In the above reaction formula, $R_2$, $R_4$ and M are as defined above.

The properties of the alkali metal salt of the imidazole-dithiocarboxylic acid are as follows.

Each compound is an alkaline glutinous solid which is easily soluble in a polar solvent such as water and alcohol and shows a reddish brown color. Recrystallization is ordinarily difficult.

The alkali metal salt is used as a precursor of an ester of the dithiocarboxylic acid which has a latent utility as an agricultural chemical, an epoxy curing agent or a rubber vulcanizer or as a precursor of a metal salt of the dithiocarboxylic acid which has a latent utility as an agricultural chemical.

When the alkali metal salt is used as the abovementioned precursor, since purification can be done in the latter stage, purification of the alkali metal salt per se is not particularly important.

If purification is particularly necessary, as described hereinbefore, the alkali metal salt is once converted to the imidazole-dithiocarboxylic acid by the acidifying treatment, the dithiocarboxylic acid is dissolved in an aqueous solution containing an equivalent amount of an alkali metal hydroxide and the aqueous solution is concentrated to the solid under reduced pressure to obtain the intended compound in the purified form. According to this method, purification can be accomplished more easily than according to the recrystallization method.

Results of thin layer chromatography (TLC) (using silica gel and ethyl alcohol) of various alkali metal salts of imidazole-dithiocarboxylic acids are described below. Spots are reddish brown and can be seen with the naked eye.

Sodium imidazole-4(5)-dithiocarboxylate of the following formula:

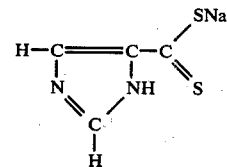

Rf: 0.0 (B.T.B.), 0.45–0.60 (observed with naked eye)

Sodium 2-methylimidazole-4(5)-dithiocarboxylate of the following formula:

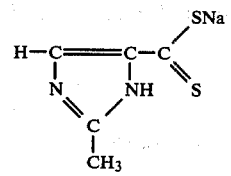

Rf: 0.0 (derived from Na, B.T.B. coloration), 0.50–0.60 (observed with naked eye)

Sodium 2-ethylimidazole-4(5)-dithiocarboxylate of the following formula:

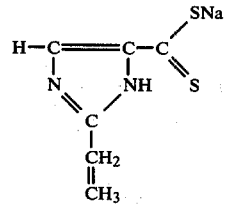

Rf: 0.0 (B.T.B.), 0.63–0.77 (observed with naked eye)

Sodium 2-undecylimidazole-4(5)-dithiocarboxylate of the following formula:

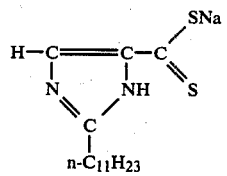

Rf: 0.0 (B.T.B.), 0.57–0.70 (observed with naked eye)

Sodium 2-heptadecylimidazole-4(5)-dithiocarboxylate of the following formula:

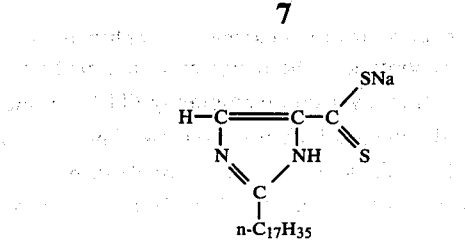

Rf: 0.0 (B.T.B.), 0.63–0.75 (observed with naked eye)

Sodium 2-phenylimidazole-4(5)-dithiocarboxylate of the following formula:

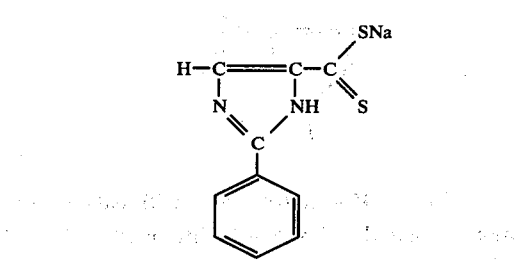

Rf: 0.0 (B.T.B.), 0.52–0.66 (observed with naked eye)

Sodium 4-methylimidazole-5-dithiocarboxylate of the following formula:

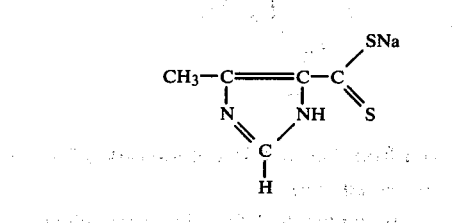

Rf: 0.0 (B.T.B.), 0.44–0.58 (observed with naked eye)

Sodium 2,4-dimethylimidazole-5-dithiocarboxylate of the following formula:

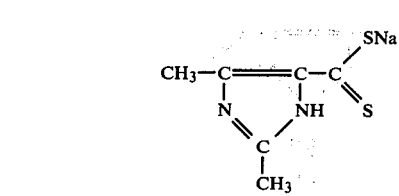

Rf: 0.0 (B.T.B.), 0.55–0.68 (observed with naked eye)

Potassium 2-ethyl-4-methylimidazole-5-dithiocarboxylate of the following formula:

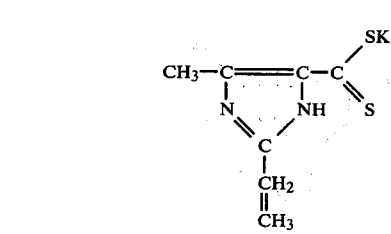

Rf: 0.0 (B.T.B.), 0.60–0.73 (observed with naked eye)

Sodium 2-undecyl-4-methylimidazole-5-dithiocarboxylate of the following formula:

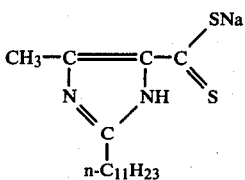

Rf: 0.0 (B.T.B.), 0.78–0.90 (observed with naked eye)

Sodium 2-phenyl-4-methylimidazole-5-dithiocarboxylate of the following formula:

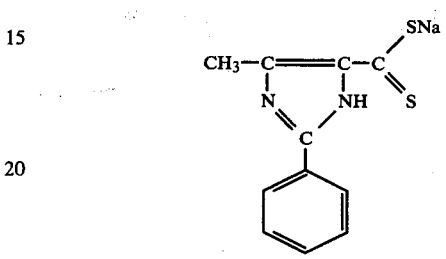

Rf: 0.0 (B.T.B.), 0.62–0.74 (observed with naked eye)

Each of the above-mentioned alkali metal salts shows a strong absorption of $\nu C=S$ at a wave number of 950 to 1030 cm$^{-1}$ in the infrared absorption spectrography.

The properties of imidazole-dithiocarboxylic acids are as follows.

Imidazole-4(5)-dithiocarboxylic acid of the following formula:

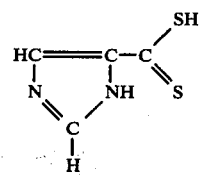

Reddish brown, neutral, melting point of 157°–159° C., hardly soluble in water, methanol, chloroform, acetone and acetic acid, easily soluble DMF, DMSO and aqueous NaOH TLC (silica gel and ethyl alcohol, observed with naked eye): Rf 0.45–0.60.

$\nu_{cm^{-1}}^{KBR}$: 1438 (second absorption), 1025 (first absorption, $\nu C=S$)

NMR (nuclear magnetic resonance) (DMSO-d$_6$): $\delta$8.80 (d, 1H, proton at 2-position), $\delta$7.78 (d, 1H, proton at 4-position)

Mass (mass spectrography): m/e 144 (M$^+$), 111 (M$^+$—SH, 68(imidazole)), 44 (C=S) 2-Methylimidazole-4(5)-dithiocarboxylic acid of the following formula:

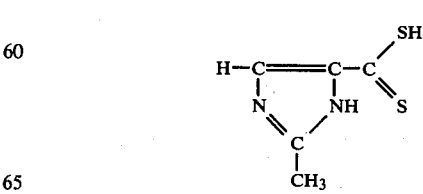

Reddish brown, neutral, melting point of 187°–188° C., hardly soluble in water, methanol, chloroform, acetone, acetic acid, acetonitrile and pyridine, easily soluble in DMSO, DMF and aqueous NaOH TLC (silica gel, ethyl alcohol, observed with naked eye): Rf 0.50–0.60

$\nu_{cm^{-1}}^{KBr}$: 1607 (third absorption, $\nu C=N$), 1210 (first absorption), 1040 (second absorption ($\nu C=S$)

NMR (DMF-$d_7$): $\delta 7.75$ (s, 1H, proton at 4-position), $\delta 2.67$ (s, 3H, methyl at 2-position)

Mass: m/e 158 (M+), 125 (M+—SH), 81 (2-methylimidazole-H),

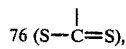

44 (C=S)

2-Ethylimidazole-4(5)-dithiocarboxylic acid of the following formula:

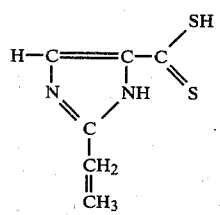

Reddish brown, neutral, melting point of 137°–139° C., hardly soluble in water, chloroform and acetic acid, easily soluble in methanol, DMSO and aqueous NaOH TLC (silica gel, ethanol, observed with naked eye): Rf 0.64–0.77

$\nu_{cm^{-1}}^{KBr}$: 1605 (second absorption, $\nu C=N$), 1045 (first absorption, $\nu C=S$)

NMR (DMSO-$d_6$): $\delta 7.70$ (s, 1H, proton at 4-position), $\delta 2.87$ (q, 2H, methyl proton of ethyl group at 2-position), $\delta 1.24$ (t, 3H, methyl proton of ethyl group at 2-position)

Mass: m/e, 172 (M+), 139 (M+—SH), 96 (2-ethylimidazole), 95 (2-ethylimidazole-H), 44 (C=S)

2-Undecylimidazole-4(5)-dithiocarboxylic acid of the following formula:

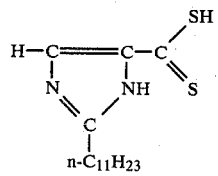

Brown, neutral, melting point of 116°–119° C., hardly soluble in water, chloroform and cold acetic acid, easily soluble in DMSO, DMF and aqueous NaOH TLC (silica gel, ethanol, observed with naked eye): Rf 0.70–0.81

$\nu_{cm^{-1}}^{KBr}$: 1602 (fourth absorption, $\nu C=N$), 1205 (third absorption), 1042 (first absorption, $\nu C=S$)

NMR (CF$_3$COOH): $\delta 7.98$ (s, 1H, proton at 4-position), $\delta 3.10$ (t, 2H, $\alpha$-methylene of undecyl group), $\delta 1.88$ (m, 2H, $\beta$-methylene of undecyl group), $\delta 1.30$ (m, 16H, intermediate methylene of undecyl group), $\delta 0.87$ (m, 3H, terminal methylene of undecyl group)

Mass: m/e (M+), 265 (M+—SH), 233 (M+—S$_2$—H), 223 (imidazole+H), 44 (C=S)

2-Heptadecylimidazole-4(5)-dithiocarboxylic acid of the following formula:

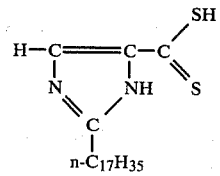

Brown, neutral, melting point of 107°–112° C., hardly soluble in water, chloroform and cold acetic acid, soluble in DMSO TLC (silica gel, ethanol, observed with naked eye): Rf 0.63–0.75

$\nu_{cm^{-1}}^{KBr}$: 1600 (first absorption, $\nu C=N$), 1525 (third absorption), 1040 (second absorption, $\nu C=S$)

NMR (DMSO-$d_6$): $\delta 7.7$ (s, 1H, proton at 4-position), $\delta 2.80$ (m, 2H, $\alpha$-methylene of heptadecyl group), $\delta 1.65$ (m, 2H, $\beta$-methylene of heptadecyl group), $\delta 1.22$ (m, 28H, intermediate methylene of heptadecyl group), $\delta 0.85$ (m, 3H, terminal methyl of heptadecyl group)

Mass: m/e, M+ does not appear, 348 (M+—H—HS), 334 (M+—HS—CH$_3$), 317 (M+—HS—S), 307 (imidazole+H), 306 (imidazole), 44 (C=S)

2-Phenylimidazole-4(5)-dithiocarboxylic acid of the following formula:

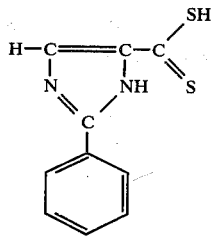

Brown crystal, weakly acidic, melting point of 154°–157° C., hardly soluble in water, methanol, chloroform, acetic acid and acetone, easily soluble in DMSO and aqueous NaOH TLC (silica gel, ethanol, observed with naked eye): Rf 0.52–0.66

$\nu_{cm^{-1}}^{KBr}$: 1615 (second absorption), 1215 (third absorption), 1040 (first absorption, $\nu C=S$)

NMR (DMSO-$d_6$): $\delta 8.33$–7.92 (m, 2H, phenyl proton), $\delta 7.92$ (s, 1H, proton at 4-position), $\delta 7.76$–7.30 (m, 3H, phenyl proton)

Mass: m/e 220 (M+), 187 (M+—SH), 144 (2-phenylimidazole), 104 (Ph—C=NH), 77 (phenyl)

4-Methylimidazole-5-dithiocarboxylic acid of the following formula:

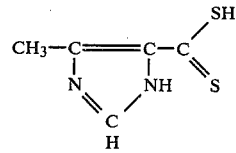

Reddish brown crystal, neutral, melting point of 159°–161° C., hardly soluble in water, methanol, chloroform and acetic acid, easily soluble in DMSO and aqueous NaOH TLC (silica gel, ethanol, observed with naked eye) Rf 0.47–0.60

$\nu_{cm^{-1}}^{KBr}$: 1590, 1440, 1375, 1265 (second absorption), 1120, 1020 ($\nu C{=}S$), 925, 860, 800, 720

NMR (DMSO-d$_6$): δ8.60 (s, 1H, proton at 2-position), δ2.62 (s, 3H, methyl proton)

Mass: m/e, 158 (M+), 125 (M+—SH), 81 (4-methylimidazole-H), 76 (—CS$_2$), 44 (C${=}$S)

2,4-Dimethylimidazole-5-dithiocarboxylic acid of the following formula:

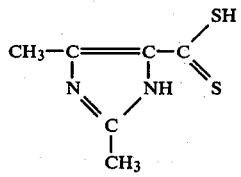

Red crystal, melting point of 187°–189° C., hardly soluble in water, methanol, ethanol, chloroform and acetone, easily soluble in DMF and DMSO TLC (silica gel, ethanol, observed with naked eye): Rf 0.57–0.70

$\nu_{cm^{-1}}^{KBr}$: 1615 (second absorption, $\nu C{=}N$), 1025, 990 (first absorption, $\nu C{=}S$)

NMR (CF$_3$COOH): δ2.77 (s, 3H, methyl proton at 2-position), δ2.70 (s, 3H, methyl proton at 4-position)

Mass: m/e, 172 (M+), 139 (M+—SH), 95 (M+—SH—CS), 42 (CH$_3$—C${=}$NH)

2-Ethyl-4-methylimidazole-5-dithiocarboxylic acid of the following formula:

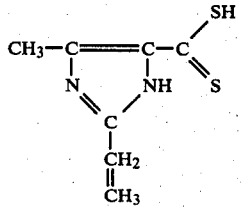

Reddish violet crystal, neutral, melting point of 177°–178.5° C., hardly soluble in water, methanol, ethanol and acetone, soluble in acetic acid, easily soluble in DMF and DMSO TLC (silica gel, ethanol, observed with naked eye): Rf 0.60–0.70

$\nu_{cm^{-1}}^{KBr}$: 1615 (second absorption, $\nu C{=}N$), 1013 (first absorption, $\nu C{=}S$)

NM (DMSO-d$_6$): δ2.80 (q, 2H, methylene proton of ethyl group at 2-position), δ2.60 (s, 3H, methyl at 4-position), δ1.23 (t, 3H, methyl proton of ethyl group at 2-position)

Mass: m/e, 186 (M+), 153 (M+—SH), 138 (M+—SH—CH$_3$), 109 (2-ethyl-4-methylimidazole-H)

2-Undecyl-4-methylimidazole-5-dithiocarboxylic acid of the following formula:

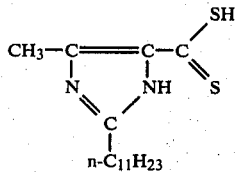

Red solid, basic, soluble in water, methanol and ethanol

TLC (silica gel, ethanol, observed with naked eye): Rf 0.7–0.8

$\nu_{cm^{-1}}^{KBr}$: 1512 (first absorption), 1378 (second absorption), 1000 (third absorption, $\nu C{=}S$)

Mass: m/e, 312 (M+), 279 (M+—HS), 247 (M+—H-S—S), 236 (2-undecyl-4-methylimidazole)

2-Phenyl-4-methylimidazole-5-dithiocarboxylic acid of the following formula:

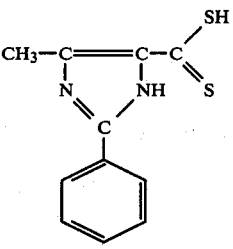

Reddish brown crystal, melting point of 165°–168° C., hardly soluble in water, methanol, ethanol, acetone, chloroform, t-butanol and benzene, soluble in acetic acid and methylcellosolve, easily soluble in DMF, DMSO, aqueous NaOH and aqueous NH$_4$OH TLC (silica gel, ethanol, observed with naked eye): Rf 0.65–0.78

$\nu_{cm^{-1}}^{KBr}$: 1625 (third absorption, $\nu C{=}N$), 1603 (phenyl), 1540 (phenyl), 1485 (phenyl), 1215 (second absorption), 1040 (first absorption, $\nu C{=}S$)

NMR (CF$_3$COOH): δ8.00–7.50 (m, 5H, phenyl), δ2.89 (s, H, methyl at 4-position)

Mass: m/e, 234 (M+), 201 (M+—SH), 158 (2-phenyl-4-methylimidazole), 104 (ph—C${=}$NH), 77 (phenyl)

An embodiment of the method for preventing rusting in metallic silver according to the present invention will now be described.

The above-mentioned dithiocarboxylic acid is dissolved in an appropriate organic solvent (for example, methanol) and the surface of surfacepolished silver is contacted with the solution (coating, spraying and dipping methods may be adopted). Then, the solvent adhering to the surface is evaporated). Even when the so-treated surface of silver is allowed to stand in air for a long time, blackening is not caused to occur at all.

In carrying out the rust preventive method of the present invention, a paste may be prepared by mixing the above-mentioned solvent solution of the dithiocarboxylic acid with an appropriate abrasive, and a rust preventive effect can be attained by polishing the surface of silver with this paste. Since this polishing treatment includes contacting the solution with the surface of silver, this method is included within the scope of the present invention.

The present invention will now be described in detail with reference to the following Examples that by no means limit the scope of the present invention.

EXAMPLE 1

A branched flask (carbon dioxide gas in air was shut off by attaching a soda lime drying tube to the flask) was charged with 0.1 mole (11 g) of 2-ethyl-4-methylimidazole and 0.1 mole (4.0 g) of NaOH, and they were heated by an alcohol lamp while removing formed water by distillation. When distillation of formed water terminated, heating was stopped and the reaction product was naturally cooled. The so-obtained sodium salt of the imidazole was solid and massive, and it was difficult to withdraw the product from the flask. Accordingly, the product was broken and pulverized promptly together with the flask and charged in a reaction vessel equipped with a reflux cooler and a soda lime tube. Then, 38 ml of t-butanol was added and the mixture was heated on an electric heater equipped with an electromagnetic stirrer until reflux started.

Then, 0.12 mole (9.1 g) of carbon disulfide was dropped into the mixture over a period of 20 minutes, and reflux was continued for 2.6 hours. Then, the reaction mixture was cooled and filtered to remove glass pieces therefrom. The filtrate was subjected to concentration under reduced pressure by a rotary evaporator to obtain a reddish brown residue (crude sodium salt). The residue was dissolved in 200 ml of water and active carbon was added to the solution, and the solution was filtered. Hydrochloric acid was added to the filtrate until the filtrate was sufficiently acidic. The precipitated crystal was recovered by filtration, washed with water and dried to obtain 12.3 g (the yield being 66% based on the imidazole) of crude 2-ethyl-4-methylimidazole-5-dithiocarboxylic acid (having a melting point of 170°–172° C.).

EXAMPLE 2

In a branched flask from which carbon dioxide gas in air was shut off by a soda lime tube, 0.05 mole (5.5 g) of 2-ethyl-4-methylimidazole and 0.05 mole (2.0 g) of NaOH were heated by an alcohol lamp while removing formed water by disillation. When distillation of formed water terminated, the flask was tilted and the sodium salt in the molten state was transferred to another reaction vessel, and the residual sodium salt was dissolved in a small amount of dimethylsulfoxide (DMSO) and the solution was transferred to the reaction vessel.

Then, 19 ml of DMSO and 0.05 mole (2.0 g) of NaOH were charged into the reaction vessel, and the mixture was heated in the same manner as described in Example 1 so that the inside temperature was 80° to 85° C. Then, 0.06 mole (4.6 g) of carbon disulfide was added dropwise over a period of 20 minutes and the mixture was maintained at 80° to 85° C. for 2.6 hours. Then, the reaction mixture was cooled and subjected to concentration under reduced pressure, and the residue was dissolved in 100 ml of water and active carbon was added to the solution. Then, the solution was filtered, and the filtrate was acidified by hydrochloric acid. The precipitated crystal was recovered by filtration, washed with water and dried to obtain 8.6 g (the yield was 92.5% based on the imidazole) of crude 2-ethyl-4-methylimidazole-5-dithiocarboxylic acid having a melting point of 171°–173° C.

EXAMPLE 3

A reaction vessel equipped with a reflux cooler and a soda lime tube was charged with 0.1 mole (11.0 g) of 2-ethyl-4-methylimidazole, 0.1 mole (5.6 g) of KOH and 38 ml of t-butanol, and the mixture was heated on an electric heater equipped with an electromagnetic stirrer until reflux started. Then, 0.12 mole (9.1 g) of carbon disulfide was dropped over a period of 20 minutes and reflux was continued for 2.6 hours. Then, the reaction mixture was cooled and subjected to concentration under reduced pressure, and the residue was dissolved in 100 ml of water and active carbon was added to the solution. Then, the solution was filtered and the filtrate was acidified by hydrochloric acid. The precipitated crystal was recovered by filtration, washed with water and dried to obtain 7.6 g (the yield was 41% based on the imidazole) of crude 2-ethyl-4-methylimidazole-5-dithiocarboxylic acid having a melting point of 167° to 169° C.

EXAMPLE 4

In the same manner as described in Example 3, 0.07 mole (7.7 g) of 2-ethyl-4-methylimidazole, 0.14 mole (5.6 g) of NaOH and 27 g of pyridine were heated with stirring, and the mixture was maintained at 80° to 85° C. Then, 0.084 mole (6.4 g) of carbon disulfide was dropped to the mixture over a period of 20 minutes, and the mixture was maintained at 80° to 85° C. for 2.6 hours. The reaction mixture was cooled and subjected to concentration under reduced pressure. The residue was dissolved in 140 ml of water and treated in the same manner as described in Example 3 to obtain 11.2 g (the yield was 86% based on the imidazole) of crude 2-ethyl-4-methylimidazole-5-dithiocarboxylic acid having a melting point of 170° to 172° C.

EXAMPLE 5

A mixture of 0.05 mole (5.5 g) of 2-ethyl-4-methylimidazole, 0.1 mole (4.0 g) of NaOH and 19 ml of α-picoline was maintained at 80° to 85° C. and 0.06 mole (4.6 g) of carbon disulfide was dropped thereto over a period of 20 minutes. The mixture was maintained at 80° to 85° C. for 2.6 hours and the reaction mixture was subjected to concentration under reduced pressure. The residue was dissolved in 100 ml of water and treated in the same manner as described in Example 3 to obtain 7.0 g (the yield was 75% based on the imidazole) of the corresponding dithiocarboxylic acid having a melting point of 168° to 169° C.

EXAMPLE 6

Procedures of Example 5 were repeated in the same manner except that β-picoline was used instead of α-picoline, to obtain 7.8 g (the yield was 84% based on the imidazole) of the corresponding dithiocarboxylic acid having a melting point of 169° to 170° C.

EXAMPLE 7

Procedures of Example 5 were repeated in the same manner except that γ-picoline was used instead of α-picoline, to obtain 7.7 g (the yield was 83% based on the imidazole) of the corresponding dithiocarboxylic acid having a melting point of 168° to 169° C.

EXAMPLE 8

Procedures of Example 5 were repeated in the same manner except that aldehydocollidine was used instead of α-picoline, to obtain 7.2 g (the yield was 77% based on the imidazole) of the corresponding dithiocarboxylic acid having a melting point of 169° to 171° C.

EXAMPLE 9

Procedures of Example 5 were repeated in the same manner except that acetonitrile was used instead of α-picoline, to obtain 7.6 g (the yield was 81% based on the imidazole) of the corresponding dithiocarboxylic acid having a melting point of 169° to 171° C.

EXAMPLE 10

Procedures of Example 5 were repeated in the same manner except that acetone was used instead of α-picoline and the reaction temperature was changed to 60° to 65° C., to obtain 7.4 g (the yield was 79% based on the imidazole) of the corresponding dithiocarboxylic acid having a melting point of 167° to 169° C.

EXAMPLE 11

Procedures of Example 5 were repeated in the same manner except that 2-ethyl-4-methylimidazole was used instead of α-picoline and the concentration under reduced pressure was omitted, to obtain 7.9 g (the yield was 85% based on carbon disulfide) of the corresponding dithiocarboxylic acid having a melting point of 168° to 170° C.

EXAMPLE 12

Procedures of Example 5 were repeated in the same manner except that DMSO was used instead of α-picoline and the reaction temperature was changed to 25° to 30° C., to obtain 8.4 g (the yield was 90% based on the imidazole) of the corresponding dithiocarboxylic acid having a melting point of 170° to 172° C.

EXAMPLE 13

Procedures of Example 5 were repeated in the same manner except that DMSO was used instead of α-picoline and the amount of NaOH was changed to 0.075 mole from 0.1 mole, to obtain 8.84 g (the yield was 95% based on the imidazole) of the corresponding dithiocarboxylic acid having a melting point of 171° to 173° C.

EXAMPLE 14

A mixture of 0.07 mole (5.74 g) of 2-methylimidazole, 0.14 mole (5.6 g) of NaOH and 26.6 ml of DMSO was maintained at 80° to 85° C. and 0.084 mole (6.4 g) of carbon disulfide was dropped to the mixture over a period of 20 minutes. Then, the mixture was maintained at 80° to 85° C. for 2.6 hours and the reaction mixture was subjected to concentration under reduced pressure. The residue was dissolved in 140 ml of water and treated in the same manner as described in Example 3 to obtain 8.7 g (the yield was 79% based on the imidazole) of 2-methylimidazole-4(5)-dithiocarboxylic acid having a melting point of 182° to 184° C.

EXAMPLE 15

A mixture of 0.07 mole (11.06 g) of 2-phenyl-4-methylimidazole, 0.14 mole (5.6 g) of NaOH and 26.6 ml of DMSO was maintained at 80° to 85° C. and 0.084 mole (6.4 g) of carbon disulfide was dropped to the mixture over a period of 20 minutes. Then, the mixture was treated in the same manner as described in Example 14 to obtain 15.9 g (the yield was 97% based on the imidazole) of 2-phenyl-4-methylimidazole-5-dithiocarboxylic acid having a melting point of 165° to 168° C.

EXAMPLE 16

Procedures of Example 15 were repeated in the same manner except that 0.7 mole (10.08 g) of 2-phenylimidazole was used instead of 2-phenyl-4-methylimidazole, to obtain 14.5 g (the yield was 94% based on the imidazole) of 2-phenylimidazole-4(5)-dithiocarboxylic acid having a melting point of 150° to 153° C.

EXAMPLE 17

Procedures of Example 15 were repeated in the same manner except that 0.07 mole (15.54 g) of 2-undecylimidazole was used instead of 0.07 mole of 2-phenyl-4-methylimidazole, to obtain 17.4 g (the yield was 83% based on the imidazole) of 2-undecylimidazole-4(5)-dithiocarboxylic acid having a melting point of 108° to 114° C.

EXAMPLE 18

Procedures of Example 15 were repeated in the same manner except that 0.07 mole (6.72 g) of 2,4-dimethylimidazole was used instead of 0.07 mole of 2-phenyl-4-methylimidazole, to obtain 11.1 g (the yield was 92% based on the imidazole) of 2,4-dimethylimidazole-5-dithiocarboxylic acid having a melting point of 185° to 187° C.

EXAMPLE 19

A mixture of 0.09 mole (6.12 g) of imidazole, 0.18 mole (7.2 g) of NaOH and 34 ml of DMSO was maintained at 80° to 85° C. and 0.108 mole (8.2 g) of carbon disulfide was dropped to the mixture over a period of 20 minutes. The reaction mixture was treated in the same manner as described in Example 14, to obtain 0.3 g (the yield was 2.3% based on the imidazole) of imidazole-4(5)-dithiocarboxylic acid having a melting point of 152° to 155° C.

EXAMPLE 20

Procedures of Example 19 were repeated in the same manner except that 0.09 mole (7.38 g) of 4-methylimidazole was used instead of 0.09 mole of imidazole, to obtain 3.65 g (the yield was 26% based on the imidazole) of 4-methylimidazole-5-dithiocarboxylic acid having a melting point of 151° to 154° C.

EXAMPLE 21

Procedures of Example 19 were repeated in the same manner except that 0.09 mole (8.64 g) of 2-ethylimidazole was used instead of 0.09 mole of imidazole, to obtain 9.6 g (the yield was 62% based on the imidazole) of 2-ethylimidazole-4(5)-dithiocarboxylic acid having a melting point of 134° to 138° C.

EXAMPLE 22

A mixture of 0.05 mole (5.5 g) of 2-ethyl-4-methylimidazole, 0.05 mole (2.0 g) of NaOH and 19 ml of DMSO was maintained at 80° to 85° C. and 0.06 mole (4.6 g) of carbon disulfide was dropped to the mixture over a period of 20 minutes. The reaction mixture was treated in the same manner as described in Example 14 to obtain 7.75 g (the yield was 83% based on the imidazole) of 2-ethyl-4-methylimidazole-5-dithiocarboxylic acid having a melting point of 171° to 172° C.

EXAMPLE 23

A mixture of 0.05 mole (5.5 g) of 2-ethyl-4-methylimidazole and 0.05 mole (2.0 g) of NaOH was treated in the same manner as described in Example 1 to form the corresponding sodium salt of the imidazole. The sodium salt was reacted with 0.06 mole (4.6 g) of carbon disulfide in 19 ml of DMSO to obtain 7.75 g (the yield was 83% based on the imidazole) of crude 2-ethyl-4-methylimidazole-5-dithiocarboxylic acid having a melting point of 171° to 172° C.

EXAMPLE 24

Procedures of Example 22 were reported in the same manner except that the amount of DMSO was changed to 9.5 ml from 19 ml and the amount of NaOH was changed to 0.10 mole from 0.05 mole, to obtain 8.5 g (the yield was 91% based on the imidazole) of crude 2-ethyl-4-methylimidazole-5-dithiocarboxylic acid having a melting point of 171° to 172° C.

EXAMPLE 25

Procedures of Example 19 were repeated in the same manner except that 0.09 mole (27.5 g) of 2-heptadecylimidazole was used instead of 0.09 mole of imidazole, to obtain 14.1 g (the yield was 41% based on the imidazole) of 2-heptadecylimidazole-4(5)-dithiocarboxylic acid having a melting point of 107° to 112° C.

EXAMPLE 26

2-Ethyl-4-methylimidazole-5-dithiocarboxylic acid was dissolved in methanol to form a solution having a concentration of 0.1% (wt/v).

The surface of a pure silver plate having a width of 1.5 cm and a length of 10 cm was polished and washed with acetone, and the right half portion of the surface was lightly wiped with gauze impregnated with the above solution and the silver plate was allowed to stand still in a room. The left half of the surface was gradually discolored but the right half was kept lustrous. When 30 days had passed, the left half was completely blackened while the right half was kept lustrous.

EXAMPLE 27

2-Phenyl-4-methylimidazole-5-dithiocarboxylic acid was dissolved in ethanol to form a solution having a concentration of 0.1% (wt/v), and the test was carried out in the same manner as described in Example 26. When 30 days had passed, the left half of the surface of the silver plate was completely blackened while the right half was kept lustrous.

EXAMPLE 28

2-Phenylimidazole-4(5)-dithiocarboxylic acid was dissolved in ethanol to form a solution having a concentration of 0.1% (wt/v). The test was carried out in the same manner as described in Example 26. When 30 days had passed, the left half was completely blackened while the right half was kept lustrous.

EXAMPLE 29

2-Undecylimidazole-4(5)-dithiocarboxylic acid was dissolved in methanol to form a solution having a concentration of 0.1% (wt/v). The test was carried out in the same manner as described in Example 26. When 30 days had passed, the left half was completely blackened while the right half was kept lustrous.

EXAMPLE 30

2-Undecyl-4-methylimidazole-5-dithiocarboxylic acid was dissolved in methanol to form a solution having a concentration of 0.1% (wt/v). The test was carried out in the same manner as described in Example 26. When 30 days had passed, the left half was completely blackened while the right half was kept lustrous.

EXAMPLE 31

2-Heptadecylimidazole-4(5)-dithiocarboxylic acid was dissolved in ethanol to form a solution having a concentration of 0.1% (wt/v). The test was carried out in the same manner as described in Example 26. When 30 days had passed, the left half was completely blackened while the right half was kept lustrous.

EXAMPLE 32

2-Ethylimidazole-4(5)-dithiocarboxylic acid was dissolved in ethanol to form a solution having a concentration of 0.1% (wt/v). The test was carried out in the same manner as described in Example 26. When 10 days had passed, the left half was discolored to yellowish brown while the right half was kept lustrous.

Example 33

2,4-Dimethylimidazole-5-dithiocarboxylic acid was dissolved in methanol to form a solution having a concentration of 0.1% (wt/v). The test was carried out in the same manner as described in Example 26. When 10 days had passed, the left half was discolored to yellowish brown while the right half was kept lustrous.

EXAMPLE 34

2-Methylimidazole-4(5)-dithiocarboxylic acid was dissolved in ethanol to form a solution having a concentration of 0.1% (wt/v). The test was carried out in the same manner as described in Example 26. When 10 days had passed, the left half was discolored in yellowish brown while the right half was kept lustrous.

EXAMPLE 35

4-Methylimidazole-5-dithiocarboxylic acid was dissolved in ethanol to form a solution having a concentration of 0.1% (wt/v). The test was carried out in the same manner as described in Example 26. When 10 days had passed, the left half was discolored to yellowish brown while the right half was kept lustrous.

What is claimed is:

1. A method for preventing rusting in metallic silver, which comprises applying an organic solvent solution of an imidazole-4(5)-dithiocarboxylic acid represented by the following formula:

$$R_4-C=\!\!=\!\!C-C-SH$$
$$\phantom{R_4-C}|\phantom{=\!\!=\!\!C}|\phantom{C}\|$$
$$\phantom{R_4-}N\phantom{=\!\!=\!\!C-}NH\ S$$
$$\phantom{R_4-C=\!\!=}\diagdown\!C\diagup$$
$$\phantom{R_4-C=\!\!=\!\!C}|$$
$$\phantom{R_4-C=\!\!=\!\!C}R_2$$

wherein $R_2$ stands for a hydrogen atom or a monovalent hydrocarbon group having up to 20 carbon atoms, and $R_4$ stands for a hydrogen atom or an alkyl group having up to 4 carbon atoms,
to the surface of metallic silver.

* * * * *